US00PP14242P29

(12) United States Plant Patent
Bradford

(10) Patent No.: US PP14,242 P2
(45) Date of Patent: Oct. 14, 2003

(54) NECTARINE TREE NAMED 'DIAMOND PEARL'

(50) Latin Name: *Prunus persica*
Varietal Denomination: Diamond Pearl

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/299,086

(22) Filed: Nov. 19, 2002

(51) Int. Cl.[7] ..... A01H 5/00

(52) U.S. Cl. ..... Plt./188

(58) Field of Search ..... Plt./188

(56) References Cited

U.S. PATENT DOCUMENTS

PP9,360 P 11/1995 Bradford
PP10,924 P 5/1999 Bradford

*Primary Examiner*—Bruce R. Campell
*Assistant Examiner*—W C Haas

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described approximately the second week in June, with first picking on Jun. 12, 2002. The fruit is uniformly large in size, excellent in flavor, globose in shape, clingstone in type, very firm in texture, white in flesh color, and red in skin color. The variety was developed as an open pollinated seedling of 'Candy White' (U.S. Plant Pat. No. 10,924) white flesh nectarine.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. In an effort to exhibit recessive traits, I also grow a lesser number of open pollinated seeds of each of these fruits. In my breeding grounds during the summer of 1996 I gathered open pollinated seeds from several different white flesh nectarine trees. One particular group of these seeds was collected from 'Candy White' (U.S. Plant Pat. No. 10,924), a white flesh freestone nectarine. This group of seeds, designated as "3P282 (OP)", was germinated and grown as seedlings on their own root in my greenhouse. Upon reaching dormancy these seedlings were transplanted to a cultivated area of my experimental orchard at Bradford Farms near Le Grand, Calif. in Merced County (San Joaquin Valley).

The present invention relates to a new and distinct variety of nectarine tree, which has been denominated varietally as 'Diamond Pearl'. It was selected by me during the 1999 fruiting season as a single plant from the group of open pollinated seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its parent, 'Candy White' (U.S. Plant Pat. No. 10,293) nectarine by producing nectarines that are globose in shape, firm in texture, mostly red in skin color, and white in flesh color, but is distinguished therefrom and an improvement thereon by producing fruit that is clingstone instead of freestone and that matures about 14 days earlier.

The present variety is most similar to June Pearl (U.S. Plant Pat. No. 9,360) nectarine by producing nectarines that are white in flesh color, nearly full red in skin color, clingstone in type and subacid in flavor, but is distinguished therefrom and an improvement thereon by producing fruit that is much larger in size, somewhat sweeter in flavor, globose instead of oblong in shape, and matures about six days earlier.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 15, 2002, on the original tree during its sixth growing season. All major color code designations are by reference to the Inter-Society Color Council, National Bureau of Standards. Common color names are also used occasionally.

Tree

Size: Large, reaching a height of 9' [2.74 m.] and a spread of 6' [1.83 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Original tree has a central leader system, but multiplied trees are typically pruned to vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

*Size.*—Medium, with a maximum diameter of 3" [76 mm.] after the sixth growing season.

*Texture.*—Shaggy.

*Bark color.*—Grayish yellowish brown [80. gy.yBr].

*Lenticels.*—Approximate Number Per Square Inch: 12. Color: Strong orange yellow [68. s.OY]. Typical Size: 1/8" to 3/8" [3.2–9.5 mm.].

Branches:

*Size.*—Diameter of limb is 7/8" [22 mm.] measured 12" from the central leader, typical of *Prunus persica,* and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Strong yellow green [117. s.YG]. Older Wood: Moderate brown [58. m.Br].

*Lenticels.*—Approximate Number Per Square Inch: 40. Color: Moderate orange yellow [71. m.OY]. Typical size: 1/16" to 3/16" [1.6–4.8 mm.].

Leaves:

*Size.*—Medium. Average Length: 5½" [140 mm.]. Average width: 1½" [38 mm.].

*Arrangement.*—Alternate.

*Thickness.*—Medium.

*Form.*—Elliptical.

*Apex.*—Acuminate.

*Base.*—Acute, with an average base angle of 90 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 3/8" [9.5 mm.]. Average Thickness: 1/16" [1.6 mm.]. Color: Brilliant yellow green [116. brill.YG].

*Stipules.*—Number: 2 per leaf, up to 6 per growing tip. Average Length: 3/8" [9.5 mm.]. Color: Brilliant yellow green [116. brill.YG] when growing.

*Glands.*—Number: Usually 2 to 4. Position: Usually alternate, positioned on both the petiole and base of blade. Size: Medium. Form: Reniform. Color: Brilliant yellow green [116. brill.YG] on younger leaves turning Dark brown [59. d.Br] in the center with maturity.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish red [258. m.pR].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with a few double blossoms.

*Petal shape.*—Circular.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded.

*Petal color.*—Pale purplish pink [252. p.pPk].

*Anther color.*—Dark red [16. d.R] over a Brilliant orange yellow [67. brill.OY] center.

*Stigma color.*—Light greenish yellow [101. l.gY].

*Sepal color.*—Dark purplish red [259. d.pR].

*Sepal length.*—9/32" [7 mm.].

*Sepal width.*—3/16" [5 mm.].

*Average pistil length.*—¾" [19.1 mm.].

*Average stamen length.*—11/16" [17.5 mm.].

*Fragrance.*—Moderate when nectar is present.

*Blooming period.*—Medium compared with other varieties.

*Onset of bloom.*—One percent on Mar. 5, 2002.

*Date of full bloom.*—Mar. 12, 2002.

*Duration of bloom.*—One to two weeks, dependent on ambient temperature.

*Number per cluster.*—1 to 3 with single flowers most common.

FRUIT

Maturity when described: Firm ripe, Jun. 15, 2002.

Date of first picking: Jun. 12, 2002.

Date of last picking: Jun. 21, 2002.

Size: Uniform, medium.

*Average diameter axially.*—2⅞" [73 mm.].

*Average diameter across suture plane.*—2⅞" [73 mm.].

*Typical weight.*—7.1 ounces [201 grams].

Form: Uniform, moderately symmetrical, globose.

*Longitudinal section form.*—Circular.

*Transverse section through diameter.*—Circular.

Suture: A sharp groove very near the stem immediately becoming a shallow groove that extends to the apex and terminates with a slight depression just beyond the pistil point.

Ventral surface: Rounded, lipped toward the apex.

Lips: Slightly unequal.

Cavity: Flaring, slightly elongated in the suture plane, suture showing on one side, Yellowish white [92. yWhite] stem markings typical.

*Depth.*—7/16 [11.1 mm.].

*Breadth.*—7/8" [22.2 mm.].

Base: Slightly truncate.

Apex: Rounded.

Pistil point: Oblique, negligible in length, depressed within the suture.

Stem: Medium.
*Average length.*—5/16" [7.9 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Slight in wet season.
*Color.*—Very deep red [14. v.deep R] over a Strong red [12. s.R] background with Moderate orange yellow [71. m.OY] freckling toward the apex.
Flesh:
*Color.*—White [263. White] from the stone to skin with virtually no red bleeding.
*Surface of pit cavity.*—White [263. White] fibers breaking when twisted from the stone.
*Amygdalin.*—Scarce.
*Juice.*—Abundant, rich.
*Texture.*—Very firm, crisp.
*Fibers.*—Abundant, fine.
*Ripens.*—Slightly earlier toward the apex.
*Flavor.*—Subacid and sweet, typically 16 to 18 brix.
*Aroma.*—Slight.
*Eating quality.*—Excellent.

STONE

Type: Clingstone.
Form: Oval.
Hilum: Oval.
Base: Straight.
Apex: Acute, with an average tip length of 1/8" [3.2 mm.].
Sides: Equal.
Surface: Irregularly furrowed near the apex and pitted toward the base.
Ridges: Jagged toward the base.
Color: Light brown [57. l.Br].
Average pit wall thickness: 1/4" [6.4 mm.].
Average width: 1 1/8" [28.6 mm.].
Average length: 1 7/16" [36.5 mm.].
Average breadth: 3/4" [19.1 mm.].
Tendency to split: Slight.

Kernel:
*Form.*—Oval.
*Pellicle color.*—Light grayish yellowish brown [79. l.gy.yBr].
*Skin color.*—Pale yellow [89. p.Y] when freshly removed.
*Vein color.*—Not distinguishable on freshly removed kernel.
*Taste.*—Very bitter.
*Viable.*—Yes.
*Average width.*—1/2" [12.7 mm.].
*Average length.*—3/4" [19.1 mm.].
*Amygdalin.*—Abundant.

USE

Market: Fresh market and long distance shipping.
Keeping quality: Good. Fruit quality observed to remain in good condition in after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'June Pearl' (U.S. Plant Pat. No. 9,360) nectarine by producing nectarines that are white in flesh color, nearly full red in skin color, clingstone in type and subacid in flavor, but is distinguished therefrom and an improvement thereon by by producing fruit that is much larger in size, somewhat sweeter in flavor, globose instead of oblong in shape, and matures about six days earlier.

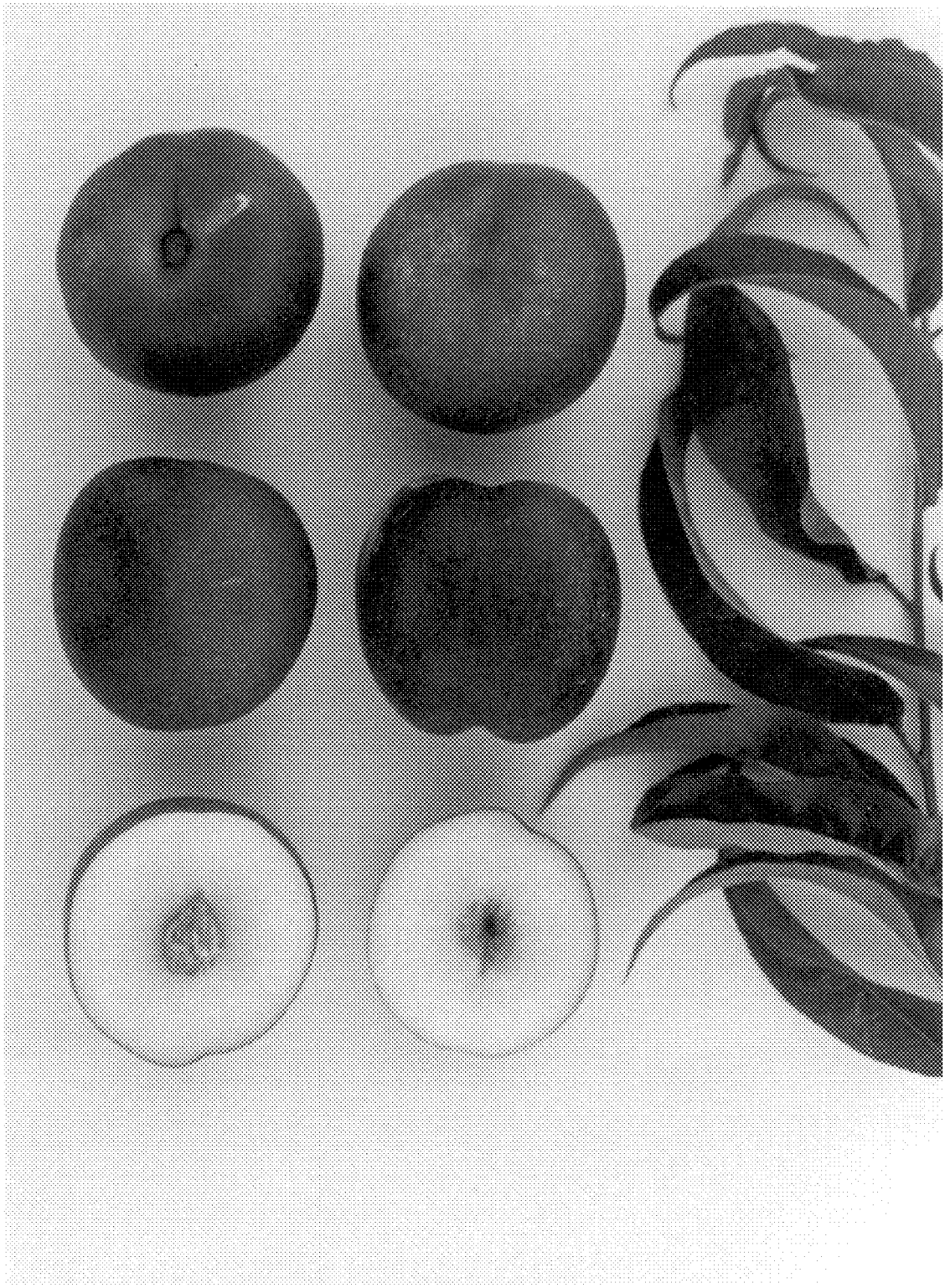

* * * * *